(12) United States Patent
Vaino et al.

(10) Patent No.: US 9,181,286 B2
(45) Date of Patent: *Nov. 10, 2015

(54) PANTOTHENATE DERIVATIVES FOR THE TREATMENT OF NEUROLOGIC DISORDERS

(71) Applicant: Retrophin, Inc., New York, NY (US)

(72) Inventors: Andrew Vaino, San Diego, CA (US); Marek Biestek, East Rockaway, NY (US); Martin Shkreli, New York, NY (US)

(73) Assignee: Retrophin, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,173

(22) Filed: Jan. 16, 2014

(65) Prior Publication Data

US 2014/0135294 A1    May 15, 2014

Related U.S. Application Data

(62) Division of application No. 13/871,691, filed on Apr. 26, 2013, now Pat. No. 8,673,883.

(60) Provisional application No. 61/639,602, filed on Apr. 27, 2012.

(51) Int. Cl.
| | |
|---|---|
| *A61K 31/132* | (2006.01) |
| *C07F 9/09* | (2006.01) |
| *C07F 9/22* | (2006.01) |
| *C07F 9/24* | (2006.01) |
| *C07F 9/572* | (2006.01) |
| *C07F 9/6561* | (2006.01) |

(52) U.S. Cl.
CPC ............... *C07F 9/222* (2013.01); *C07F 9/2458* (2013.01); *C07F 9/5728* (2013.01); *C07F 9/09* (2013.01); *C07F 9/65616* (2013.01)

(58) Field of Classification Search
CPC ....................................................... C07F 9/09

USPC ................. 514/80, 109; 548/414; 560/81
See application file for complete search history.

(56) References Cited

PUBLICATIONS

Balibar et al., Pantethine Rescues Phosphopantothenoylcysteine Synthetase and Phosphopantothenoylcysteine Decarboxylase Deficiency in *Escherichia coli* but not *Pseudomonas aeruginosa*, Journal of Bacteriology, 2011: 3304-3312.
Hayflick et al., Unraveling the Hallervorden-Spatz Syndrome: Pantothenate Kinase-Associated Neurodegeneration is the name . . . , Current Opinion in Pediatrics, 2003, 15:572-577.
Hecker et al., Prodrugs of Phosphate and Phosphonates, J. Med. Chem., 2008, 51:2328-2345.
Hwang et al., Enzymatic and Cellular Study of a Serotonin N-acetyltransferase Phosphopantetheine-based Prodrug, Bioorganic & Medicinal Chemistry, 2007, 15:2147-2155.
International Search Report issued in PCT/US2013/038458 on Jul. 4, 2013.
Gregory et al., "Pantothenate Kinase-Associated Neurodegeneration," NCBI Bookshelf, 22 pages, accessed on Jun. 30, 2014.
Jackowski et al., "Metabolism of 4'-Phosphopantetheine in *Escherichia coli*," *Journal of Bacteriology* 158(1):115-120, 1984.
Pellecchia et al., "The diverse phenotype and genotype of pantothenate kinase-associated neurodegeneration," *Neurology* 64:1810-1812, 2005.
Garcia et al., "Germline Deletion of Pantothenate Kinases 1 and 2 Reveals the Key Roles for CoA in Postnatal Metabolism," *PLoS One* 7(7): e40871. doi: 10.1371/journal.pone.0040871, Jul. 2012, 13 pages.
Madela et al., "Progress in the development of anti-hepatitis C virus nucleoside and nucleotide prodrugs," *Future Med. Chem.* 4(5):625-650, 2012.
McGuigan et al., "Aryl Phosphoramidate Derivatives of d4T Have Improved Anti-HIV Efficacy in Tissue Culture and May Act by the Generation of a Novel Intracellular Metabolite," *J. Med. Chem.* 39:1748-1753, 1996.

*Primary Examiner* — Shawquia Jackson
(74) *Attorney, Agent, or Firm* — Seed IP Law Group PLLC

(57) ABSTRACT

The present disclosure relates to pantothenate derivatives for the treatment of neurologic disorders (such as pantothenate kinase-associated neurodegeneration), pharmaceutical compositions containing such compounds, and their use in treatment of neurologic disorders.

19 Claims, 2 Drawing Sheets

PANTOTHENATE DERIVATIVES FOR THE TREATMENT OF NEUROLOGIC DISORDERS

This application is a divisional of U.S. patent application Ser. No. 13/871,691, filed Apr. 26, 2013, which claims the benefit of U.S. Provisional Application No. 61/639,602, filed Apr. 27, 2012, the entire contents of which are hereby incorporated by reference.

FIELD OF THE INVENTION

The present invention relates to pantothenate derivatives for the treatment of neurologic disorders (such as pantothenate kinase-associated neurodegeneration), pharmaceutical compositions containing such compounds, and their use in treatment of neurologic disorders.

BACKGROUND

Pantothenate kinase-associated neurodegeneration (PKAN) is a form, thought to be responsible for half, of neurodegeneration with brain iron accumulation (NBIA) that causes extrapyramidal dysfunction (e.g., dystonia, rigidity, choreoathetosis) (A. M. Gregory and S. J. Hayflick, "Neurodegeneration With Brain Iron Accumulation", *Orphanet Encyclopedia*, September 2004). PKAN is thought to be a genetic disorder resulting from lack of the enzyme pantothenate kinase, which is responsible for the conversion of pantothenate (vitamin B-5) to 4'-phosphopantothenate. 4'-Phosphopantothenate is subsequently converted into Coenzyme A (CoA) (as shown below) (R. Leonardi, Y.-M. Zhang, C. O. Rock, and S. Jackowski, "Coenzyme A: Back In Action", *Progress in Lipid Research*, 2005, 44, 125-153).

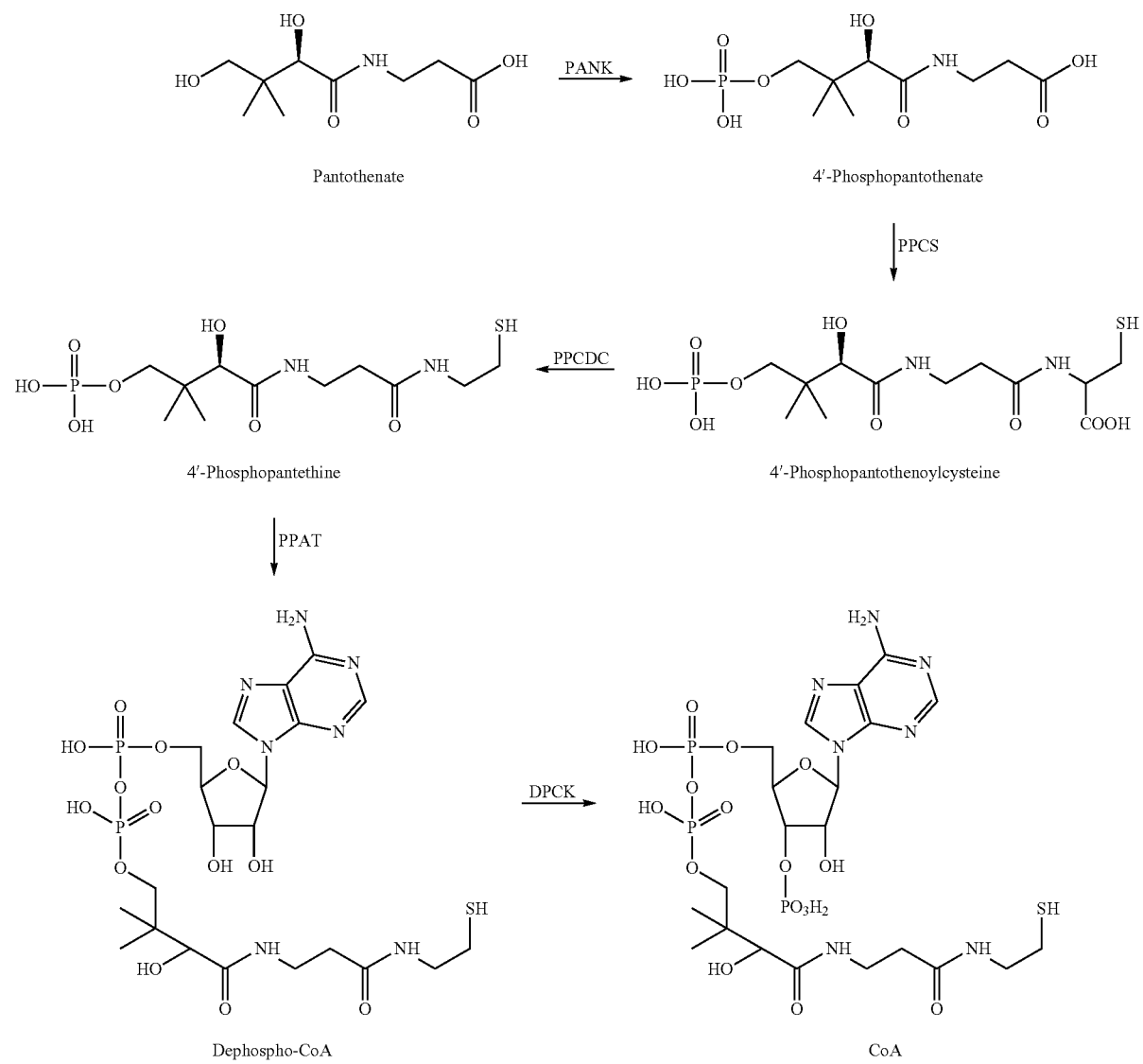

In particular, pantothenate is converted to 4'-phosphopantothenate via the enzyme pantothenate kinase (PANK), which is converted to 4'-phosphopantothenoylcysteine via the enzyme 4'-phosphopantothenoylcysteine synthase (PPCS), and subsequently decarboxylated to 4'-phosphopantethine via 4'-phosphopantothenoylcysteine decarboxylase (PPCDC). 4'-phosphopantethine is then appended to adenosine by the action of phosphosphpantethine adenyltransferease (PPAT) to afford dephospho CoA, which is finally converted to coenzyme A (CoA) via dephospho-CoA kinase (DPCK).

Classic PKAN usually presents in a child's first ten to fifteen years, though there is also an atypical form that can occur up to age 40. PKAN is a progressively degenerative disease, that leads to loss of musculoskeletal function with a devastating effect on quality of life.

One approach to treating PKAN could be to use the product of the enzymic reaction, namely, 4'-phosphopantothenate. This approach has been mentioned in the literature, but it has been recognized that the highly charged molecule would not be able to permeate the lipohilic cell membrane (C. J. Balibar, M. F. Hollis-Symynkywicz, and J. Tao, "Pantethine Rescues Phosphopantothenoylcysteine Synthetase And Phosphopantothenoylcysteine Decarboxylase Deficiency In *Escherichia Coli* But Not In Pseudomonas Aeruginosa", *J. Bacteriol.*, 2011, 193, 3304-3312).

SUMMARY OF THE INVENTION

The present invention relates to prodrugs of 4'-phosphopantothenate or a surrogate for 4'-phosphopantothenate. These prodrugs have greater cell permeability than 4'-phosphopantothenate. Without wishing to be bound by any particular theory, it is believed that the replacement of 4'-phosphopantothenate, or the use of a surrogate for it, will permit the body to synthesize CoA or an active variant of it. Thus, these prodrugs are useful for treating disorders resulting from a deficiency of 4'-phosphopantothenate and/or CoA.

One embodiment of the present invention is a prodrug of 4'-phosphopantothenate (3-{[(2R)-2-hydroxy-3,3-dimethyl-4-(phosphonooxy)butanoyl]amino}propanoic acid). The prodrug may have one or more prodrug moieties attached to the 4'-phosphopantothenate. Preferably, these prodrug moieties reduce the charge of the compound thereby enhancing its cell permeability. In one embodiment, one or more prodrug moieties are attached to the carboxyl group and/or the phosphono group of the 4'-phosphopantothenate. In a preferred embodiment, the prodrug has one prodrug moiety bound to the carboxyl group and two prodrug moieties attached to the phosphono group. In one more preferred embodiment, the hydrogen on one hydroxyl group of the phosphono moiety is replaced with a prodrug moiety, and the other hydroxyl group of the phosphono moiety is replaced with an amino group (e.g., an amino acid, attached through its amino group to the phosphorous atom).

In one embodiment, the present invention relates to a prodrug of 4'-phosphopantothenate or other compound of the present invention that does not form an ion at physiological pH (e.g., at a pH of between about 7.3 and about 7.5, such as at a pH of between about 7.3 and about 7.4, such as at a pH of about 7.4 or at a pH of about 7.365).

In another embodiment, the present invention relates to a prodrug of 4'-phosphopantothenate or other compound of the present invention having a pKa value of about 7.

Another embodiment of the present invention is a compound having the formula:

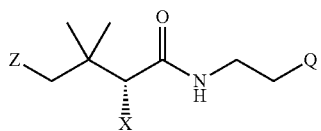

or a pharmaceutically acceptable salt thereof, wherein

X is hydroxy, halogen, —$OR^6$, or —$SR^6$ (where $R^6$ is a $C_1$-$C_6$ alkyl, $C_2$-$C_6$ alkenyl, or $C_2$-$C_6$ alkynyl, such as methyl, ethyl, n-propyl, i-propyl, n-butyl, s-butyl);

Q is a carboxylic acid (—COOH), a sulfinic acid (—SOOH), a sulfonic acid (SOOOH), or an ester thereof (i.e., —$COOR^1$, —$SOOR^1$, —$SOOOR^1$);

$R^1$ is selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl;

(a) Z is a phosphonate (—$CH_2P(O)OR^2$), phosphate (—$OP(O)OR^3R^4$), a thiophosphonate (—$CH_2P(S)OR^2$), a thiophosphate (—$OP(S)OR^3R^4$),

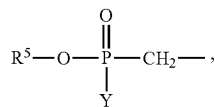

Formula B

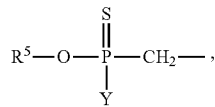

Formula C

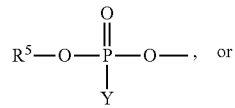

Formula D

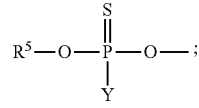

Formula E $R^2$, $R^3$, and $R^4$ are independently selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl;

$R^5$ is selected from substituted or unsubstituted $C_1$-$C_6$ alkyl (such as unsubstituted $C_1$-$C_6$ alkyl), substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl;

Y is a natural or unnatural amino acid ester of the formula

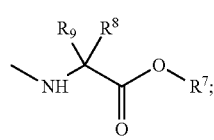

Formula F $R^7$ is selected from substituted or unsubstituted $C_1$-$C_6$ alkyl (such as unsubstituted $C_1$-$C_6$ alkyl), substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl;

$R^8$ and $R^9$ are independently selected from hydrogen, amino acid side chains, $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl;

with the proviso that $R^8$ and $R^9$ are not both hydrogen.

In one preferred embodiment, the amino acid side chain in the definition of $R^8$ and $R^9$ is that of a natural amino acid (e.g., an L-amino acid). In formula F, $R^8$ and $R^9$ may be attached to the carbon depicted such that the carbon has the R or S absolute configuration (D or L relative configuration). In a more preferred embodiment, one of $R^8$ and $R^9$ is hydrogen and the other is an amino acid side chain (preferably, an amino acid side chain of a natural L-amino acid, such as a proteinogenic amino acid).

Another embodiment is a compound having the formula:

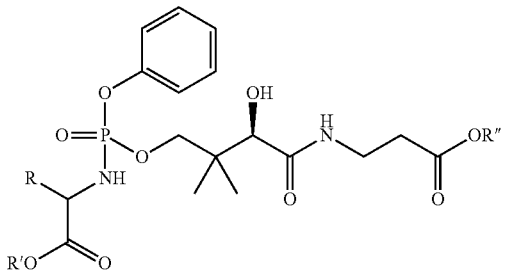

Formula G or a pharmaceutically acceptable salt thereof, wherein
R is an amino acid side chain;
R' is selected from $C_1$-$C_6$ alkyl substituted or unsubstituted $C_1$-$C_6$ alkyl (such as unsubstituted $C_1$-$C_6$ alkyl), substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl; and R" is selected from substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_8$ cycloalkyl, substituted or unsubstituted $C_3$-$C_8$ cycloalkenyl, substituted or unsubstituted $C_3$-$C_8$ cycloalkyl ($C_1$-$C_6$ alkyl), substituted or unsubstituted $C_3$-$C_8$ cycloalkenyl($C_1$-$C_6$ alkyl), substituted or unsubstituted aryl, substituted or unsubstituted arylalkyl, substituted or unsubstituted heterocyclyl, substituted or unsubstituted heteroaryl, substituted and unsubstituted heterocyclylalkyl, and substituted and unsubstituted heteroarylalkyl.

In one preferred embodiment, the amino acid side chain in the definition of R is that of a natural amino acid (e.g., a natural L-amino acid). R may be attached to the carbon depicted such that the carbon has the R or S absolute configuration (D or L relative configuration). In a more preferred embodiment, R is the side chain of a proteinogenic amino acid. In one preferred embodiment, the stereochemistry of the R group is such that the molecule has the following stereochemistry:

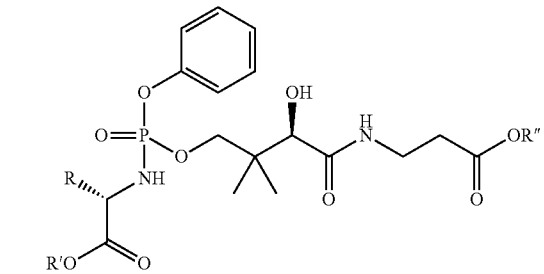

In one embodiment of the compound of formula G, R' is $C_1$-$C_6$ alkyl (e.g., methyl, ethyl, n-propyl, i-propyl, n-butyl, i-butyl, t-butyl), benzyl, cyclohexyl, and methylcyclopropyl.

In one embodiment of the compound of formula G, R" is $C_1$-$C_6$ alkyl (e.g., methyl, ethyl, n-propyl, i-propyl, n-butyl, i-butyl, t-butyl), benzyl, cyclohexyl, and methylcyclopropyl.

Another embodiment is a compound having the formula:

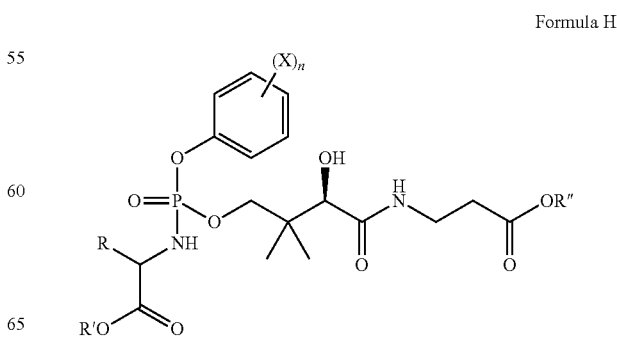

Formula H or a pharmaceutically acceptable salt thereof, wherein
R is an amino acid side chain;
X is halogen (e.g., F);
n is 0, 1, 2, 3, 4 or 5 (e.g., 0, 1 or 2);
R' is selected from $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_3$-$C_8$ cycloalkyl($C_1$-$C_6$ alkyl), $C_3$-$C_8$ cycloalkenyl($C_1$-$C_6$ alkyl), aryl, arylalkyl, heterocyclyl, heteroaryl, heterocyclylalkyl, and heteroarylalkyl; each of which is optionally substituted by one or more halogen (e.g., fluorine); and
R" is selected from $C_1$-$C_6$ alkyl, $C_2$-$C_6$ alkenyl, $C_2$-$C_6$ alkynyl, $C_3$-$C_8$ cycloalkyl, $C_3$-$C_8$ cycloalkenyl, $C_3$-$C_8$ cycloalkyl($C_1$-$C_6$ alkyl), $C_3$-$C_8$ cycloalkenyl($C_1$-$C_6$ alkyl), aryl, arylalkyl, heterocyclyl, heteroaryl, heterocyclylalkyl, and heteroarylalkyl; each of which is optionally substituted by one or more halogen (e.g., fluorine).

In one preferred embodiment, n is 0. In another preferred embodiment n is 1.

In one preferred embodiment, the amino acid side chain in the definition of R is that of a natural amino acid (e.g., a natural L-amino acid). R may be attached to the carbon depicted such that the carbon has the R or S absolute configuration (D or L relative configuration). In a more preferred embodiment, R is the side chain of a proteinogenic amino acid. In one preferred embodiment, the stereochemistry of the R group is such that the molecule has the following stereochemistry:

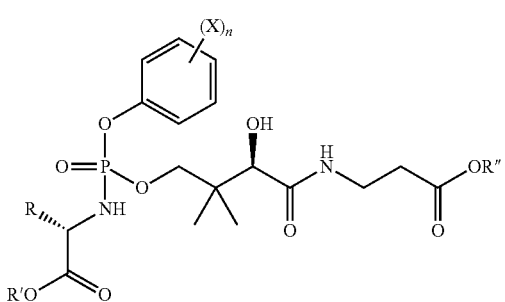

In one embodiment of the compound of formula H, R' is $C_1$-$C_6$ alkyl (e.g., methyl, ethyl, n-propyl, i-propyl, n-butyl, i-butyl, or t-butyl), benzyl, cyclohexyl, or methylcyclopropyl, each of which is optionally substituted by one or more halogen (e.g., fluorine).

In one embodiment of the compound of formula H, R" is $C_1$-$C_6$ alkyl (e.g., methyl, ethyl, n-propyl, i-propyl, n-butyl, i-butyl, or t-butyl), benzyl, cyclohexyl, or methylcyclopropyl, each of which is optionally substituted by one or more halogen (e.g., fluorine).

Preferred compounds of the present invention include those having the formula:

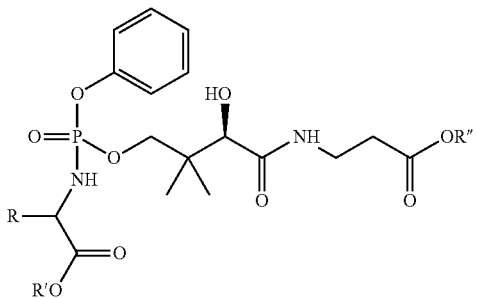

or a pharmaceutically acceptable salt thereof, wherein

| R (AA) | R' | R" |
| --- | --- | --- |
| L-Ala | Et | Et |
| L-Ala | Me | Me |
| L-Ala | n Bu | n Bu |
| L-Ala | Bn | Et |
| L-Ala | Et | Bn |
| L-Ala | Bn | Bn |
| L-Ala | MeCyPr | MeCyPr |
| Gly | Et | Et |
| Gly | Bn | Bn |
| Gly | Bn | Et |
| Gly | Et | Bn |
| L-Val | Et | Et |
| L-Trp | Me | Me |
| L-Trp | Et | Et |
| L-Trp | Bn | Et |
| L-Trp | Et | Bn |
| L-Trp | Bn | Bn |

(wherein Bn is benzyl, Cy is cyclohexyl, Et is ethyl, hex is hexyl, iBu is isobutyl, iPr is isopropyl, Me is methyl, MeCyPr is methylcyclopropyl (i.e., —$CH_2$-cyclopropyl, and MeIndole is (1H-indol-3-yl)methyl). In one embodiment, the compounds mentioned above have the following stereochemistry:

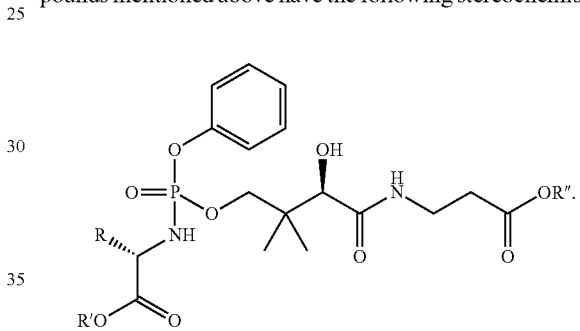

Yet another embodiment is a pharmaceutical composition comprising a compound of the present invention, and a pharmaceutically acceptable excipient. In one embodiment, the pharmaceutical composition includes an effective amount of the compound to treat a neurologic disorder. The pharmaceutical composition may be a dosage unit form, such as a tablet or capsule.

Yet another embodiment is a method of treating a disorder associated with a deficiency of pantothenate kinase, 4'-phosphopantothenate, or Coenzyme A in a subject. The method comprises administering to the subject an effective amount of a compound of the present invention.

Yet another embodiment is a method of treating pantothenate kinase-associated neurodegeneration in a subject. The method comprises administering to the subject an effective amount of a compound of the present invention. The subject may suffer from neurodegeneration with brain iron accumulation.

Yet another embodiment is a method of treating Parkinson's disease in a subject. The method comprises administering to the subject an effective amount of a compound of the present invention.

Yet another embodiment is a method of treating cells or tissue involved in a pathology characterized by abnormal neuronal function in a subject. The method comprises administering to the subject an effective amount of a compound of the present invention. The pathology may be selected from dystonia, extrapyramidal effects, dysphagia, rigidity and/or stiffness of limbs, choreoathetosis, tremor, dementia, spasticity, muscle weakness, and seizure.

Yet another embodiment is a method of treating cells or tissues involved in a pathology characterized by dysfunctional neuronal cells caused by misregulation of the gene associated with the enzyme pantothene kinase. The method comprises administering to the subject an effective amount of a compound of the present invention.

Yet another embodiment is a method of treating a pathology characterized by dysfunctional neuronal cells caused by misregulation of the gene associated with the enzyme pantothene kinase in a subject. The method comprises administering to the subject an effective amount of a compound of the present invention.

Yet another embodiment is a method of treating cells or tissues involved in a pathology characterized by dysfunctional neuronal cells caused by misregulation of the expression of the gene associated with the enzyme pantothene kinase. The method comprises administering to the subject an effective amount of a compound of the present invention.

Yet another embodiment is a method of treating a pathology characterized by dysfunctional neuronal cells caused by misregulation of the expression of the gene associated with the enzyme pantothene kinase in a subject. The method comprises administering to the subject an effective amount of a compound of the present invention.

Yet another embodiment is a method of treating a subject having neuronal cells with an over accumulation of iron. The method comprises administering to the subject an effective amount of a compound of the present invention.

In the aforementioned methods, the subject may be a child (for example, 10 to 15 years old) or an adult.

Yet another embodiment is a method of preparing a compound of formula G or H by:

(a) protecting both hydroxyl groups of pantothenic acid;
(b) esterifying the acid moiety of the protected pantothenic acid to form a compound of the formula:

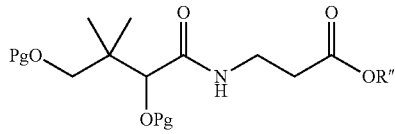

where each Pg independently represent a protecting group, and R" is defined as above with respect to formula G or H;

(c) deprotecting the hydroxyl groups;
(d) phosphorylating the deprotected compound with a compound of the formula:

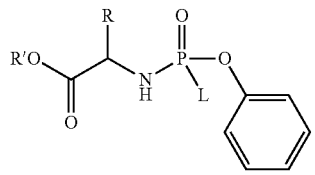

wherein L is a leaving group (e.g., halogen such as chloro), and R and R' are defined as above with respect to formula G or H; and (e) optionally, forming a salt of the compound formed in step (d).

Yet another embodiment is a method of preparing a compound of formula G or H by:

(a) esterifying pantothenic acid with an alcohol of the formula R"OH to form a compound of the formula:

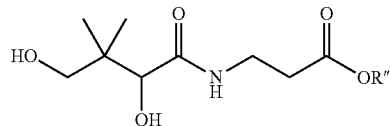

wherein R" is defined as above with respect to formula G or H;

(b) phosphorylating the esterified compound with a compound of the formula:

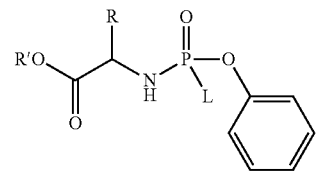

wherein L is a leaving group (e.g., halogen), and R and R' are defined as above with respect to formula G or H; and (c) optionally, forming a salt of the compound formed in step (b). The esterification in step (a) can be performed by subjecting pantothenic acid to Fischer esterification conditions.

DETAILED DESCRIPTION OF THE INVENTION

Definitions

Figure 1:
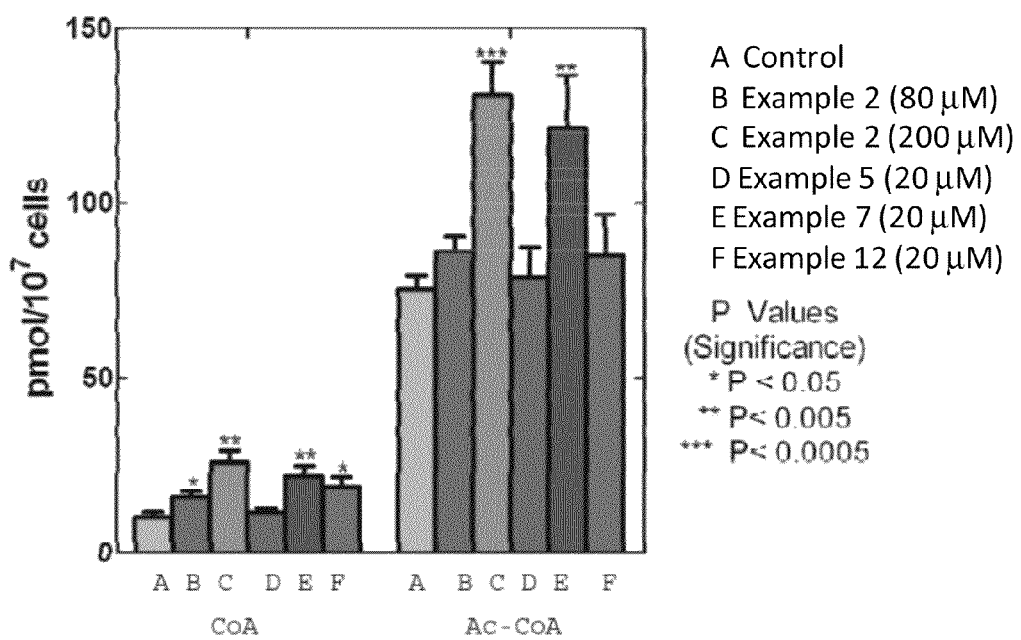
FIG. 1 is a bar graph showing the levels of acetyl CoA in human HEK 293T cells, as measured by mass spectrometry, following treatment with the compounds of Examples 2, 5, 7 and 12.

As used herein, certain items may have the following define meanings.

As used in the specification and claims, the singular for "a", "an", and "the" include plural references unless the context clearly dictates otherwise. For example, the term "a cell" includes a plurality of cells, including mixtures thereof. Similarly, use of "a compound" for treatment of preparation of medicaments as described herein contemplates using one or more compounds of the invention for such treatment or preparation unless the context clearly dictates otherwise.

As used herein, the term "comprising" is intended to mean that the compositions and methods include the recited elements, but not excluding others. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the composition of this invention. Embodiments defined by each of the transitional terms are within the scope of this invention.

The term "alkyl" refers to a straight or branched hydrocarbon chain radical consisting solely of carbon and hydrogen atoms, containing no unsaturation. Unless otherwise specified, the term "alkyl" refers to a group having from one to eight carbon atoms (for example, one to six carbon atoms, or one to four carbon atoms), and which is attached to the rest of the molecule by a single bond. Examples of alkyl groups include, but are not limited to, methyl, ethyl, n-propyl, i-propyl, n-butyl, t-butyl, s-butyl, n-pentyl, and s-pentyl.

The term "alkenyl" refers to an aliphatic hydrocarbon group containing a carbon-carbon double bond and which may be a straight or branched or branched chain. Unless otherwise specified, the term "alkenyl" refers to a group having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond. Unless otherwise specified, the term "alkynyl" refers to a group having in the range of 2 up to about 12 carbon atoms (for instance, 2 to 10 2 to 10 carbon atoms), e.g., ethynyl, propynyl, and butynyl.

The term "cycloalkyl" denotes a non-aromatic mono or multicyclic ring system of about 3 to 12 carbon atoms such as cyclopropyl, cyclobutyl, cyclopentyl, and cyclohexyl.

The term "cycloalkylalkyl" refers to a cyclic ring-containing radical containing in the range of about 3 up to 8 carbon atoms directly attached to an alkyl group which is then attached to the main structure at any carbon in the alkyl group that results in the creation of a stable structure such as cyclopropylmethyl, cyclobutylethyl, and cyclopentylethyl.

The term "aryl" refers to a mono- or multi-cyclic aromatic radical having in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$, and —$C_2H_5C_6H_5$.

The term "heterocyclyl" refers to a non-aromatic 3 to 15 member ring radical which, consists of carbon atoms and at least one heteroatom selected from nitrogen, phosphorus, oxygen and sulfur. The heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized.

The term "heterocyclylalkyl" refers to a heterocyclyl group as defined above directly bonded to an alkyl group as defined above.

The term "heteroaryl" refers to an optionally substituted 5-14 member aromatic ring having one or more heteroatoms selected from N, O, and S as ring atoms. The heteroaryl may be a mono-, bi- or tricyclic ring system. Examples of such heteroaryl ring radicals includes but are not limited to oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl and isoquinolyl.

The term "heteroarylalkyl" refers to an heteroaryl group as defined above directly bonded to an alkyl group as defined above, e.g., —$CH_2C_6H_4N$, and —$C_2H_5C_6H_4N$.

The term "halogen" includes F, Cl, Br, and I.

The term "amino acid side chain" refers to the side chain R of an alpha amino acid of the formula $H_2N$—CH(R)—COOH. For example, the side chain of alanine is methyl, the side chain of glycine is hydrogen, the side chain of valine is iso-propyl, and the side chain of tryptophan is (1H-indol-3-yl)methyl. Suitable amino acid side chains in the compounds of the present invention include those of natural amino acids, including proteinogenic amino acids. Non-limiting examples of natural amino acids include Standard amino acids or proteinogenic amino acids include but are not limited to alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine.

The term "substituted", unless otherwise specified, refers to substitution with any one or any combination of the following substituents: hydrogen, hydroxy, halogen, carboxyl, cyano, nitro, oxo (=O), thio(=S), alkyl, alkoxy, alkenyl, alkynyl, aryl, arylalkyl, cycloalkyl, cycloalkenyl, aryl, heterocyclyl, heteroaryl, —$COOR^x$, —$C(O)R^x$, —$C(S)R^x$, —$C(O)NR^xR^y$, —$C(O)ONR^xR^y$, —$NR^yR^z$, —$NR^xCONR^yR^z$, —$N(R^x)SOR^y$, —$N(R^x)SO_2R^y$, —(=N—N($R^x$)$R^y$), —$NR^x C(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, and —$ONO_2$, wherein $R^x$, $R^y$ and $R^z$ in each of the above groups can be hydrogen atom, alkyl, alkoxy, alkenyl, alkynyl, aryl, arylalkyl, cycloalkyl, cycloalkenyl, amino, aryl, heteroaryl, heterocyclyl, or any two of $R^x$, $R^y$ and $R^z$ may be joined to form a saturated or unsaturated 3-10 member ring, which may optionally include heteroatoms which may be same or different and are selected from O, NH or S. In one embodiment, the term substituted refers to substitution with one or more halogens (e.g., fluorine).

The term "subject" refers to a mammal, such as a domestic pet (for example, a dog or cat), or human. Preferably, the subject is a human.

The phrase "effective amount" refers to the amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Pharmaceutical Formulations and Routes of Administration

The compounds of the present invention may be administered by a variety of routes including orally and by injection (e.g. subcutaneously, intravenously, and intraperitoneally).

The compounds may be administered orally in the form of a solid or liquid dosage form. In both, the compound may be coated in a material to protect it from the action of acids and other natural conditions which may inactivate the compound. The compounds may be formulated as aqueous solutions, liquid dispersions, (ingestible) tablets, buccal tablets, troches, capsules, elixirs, suspensions, syrups, and wafers. The oral dosage forms may include excipients known in the art, such as binders, disintegrating agents, flavorants, antioxidants, and preservatives. Liquid dosage forms may include diluents such as saline or an aqueous buffer.

The compounds may also be administered by injection. Formulations suitable for injection may include sterile aqueous solutions (where water soluble) or dispersions, and sterile powders for the extemporaneous preparation of sterile injectable solutions or dispersions. The composition may be sterile and be fluid to the extent that easy syringability exists. It may be stable under the conditions of manufacture and storage and be preserved against the contaminating action of microorganisms such as bacteria and fungi. The carrier can be a solvent or dispersion medium containing, for example, water, ethanol, polyol (such as, glycerol, propylene glycol, and liquid polyethylene glycol), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, and ascorbic acid. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The actual dosage amount of the compound administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject.

In one embodiment, a human subject is administered the daily doses of from about 0.01 mg/kg to about 100 mg/kg.

Single or multiple doses of the compounds are contemplated. Desired time intervals for delivery of multiple doses can be determined by one of ordinary skill in the art employing no more than routine experimentation. As an example, subjects may be administered two doses daily at approximately 12 hour intervals. In some embodiments, the compound is administered once a day.

The compounds may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks therebetween. Alternatively, the predetermined routine schedule may involve administration on a twice daily basis for the first week, followed by a daily basis for several months. In other embodiments, the invention provides that the agent(s) may taken orally and that the timing of which is or is not dependent upon food intake. Thus, for example, the agent can be taken every morning and/or every evening, regardless of when the subject has eaten or will eat.

Combination Therapy

In addition to being used as a monotherapy, the compounds may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

The additional agent or agents may be selected from any agent or agents useful for treating a neurological disorder, for example any agent or agents useful for treating a deficiency of pantothenate kinase, 4'-phosphopantothenate, or Coenzyme A. In one embodiment, the additional agent or agent is useful in improving cognitive function, e.g., an acetylcholinesterase inhibitor, such as physostigmine, neostigmine, pyridostigmine, ambenonium, demarcarium, rivastigmine, galantamine, donezepil, and combinations thereof. In another embodiment, the additional agent or agents is an iron chelator, such as deferiprone, deferoxamine, deferasirox, and combinations thereof.

Synthesis of Phosphopantothenate Derivatives

The compounds of the present invention can be prepared from pantothenic acid (vitamin B5), which is readily available. The synthesis of pantothenic acid is described, for example, in U.S. Pat. Nos. 2,676,976 and 2,870,188.

The following synthesis for preparing the compounds of formula G can be adapted to prepare other compounds of the present invention, such as compounds of formula H. The compound of formula G can be prepared by (a) protecting both hydroxyl groups of pantothenic acid, (b) esterifying the acid moiety of the protected pantothenic acid to form a compound of the formula:

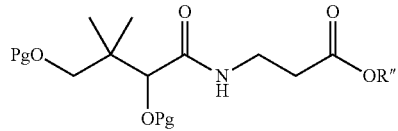

where each Pg independently represent a protecting group, and R" is defined as above with respect to formula G, (c) deprotecting the hydroxyl groups, (d) phosphorylating the deprotected compound with a compound of the formula:

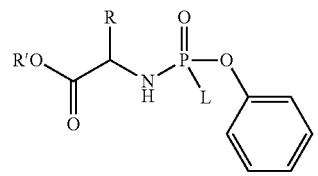

wherein L is a leaving group (e.g., halogen), and R and R' are defined as above with respect to formula G; and (e) optionally, forming a salt of the compound formed in step (d). This reaction scheme is shown below (where L is Cl):

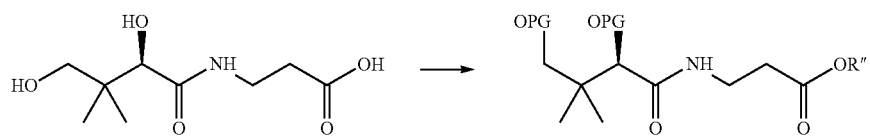

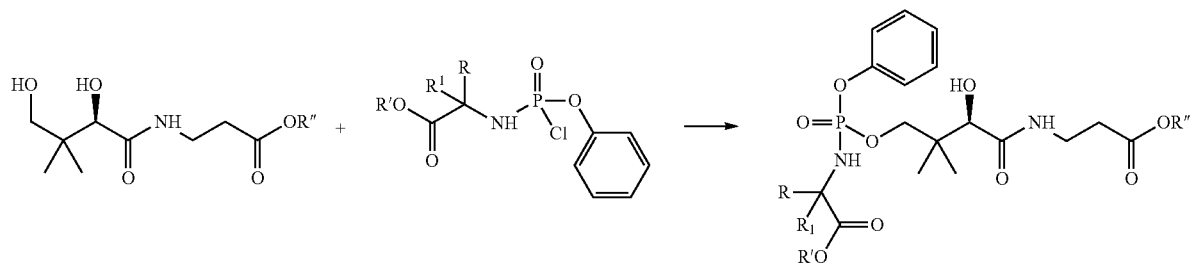

(Note: R¹ in the last step can be hydrogen.)

The protection step (a) can be performed by treating pantothenic acid with benzaldehyde and zinc chloride to afford the corresponding acetal (T. W. Green and P. G. M. Wuts, *Protective Groups in Organic Synthesis*, Wiley-Interscience, New York, 1999, 217-224, 716-719). The pantothenic acid may also be protected by treatment of pantothenic acid with acetone and toluene sulfonic acid (M. Carmack and C. J. Kelley, "Synthesis of optically active Cleland's reagent [(−)-1,4-dithio-L-threitol]", *J. Org. Chem.*, 1968, 33, 2171-2173) to afford the corresponding acetal. In another example, pantothenic acid is treated with sodium hydride followed by benzyl bromide to afford the di-O-benzylated pantothenic acid (T. W. Green et al., supra).

After diprotection of the hydroxyl groups, formation of an ester (R″) may be accomplished by, for example, reacting the diprotected pantothenic acid with an appropriate alcohol, and dicyclohexyldicarbodimide (DCC), or diethylazodicarboxylate (DEAD) and triphenylphosphine (a Mitsunobu reaction). Alternatively, the protected pantothenic acid can be converted to the corresponding acid chloride (for example, with thionyl chloride or oxalyl chloride), followed by treatment with the corresponding alcohol.

Deprotection can be performed by any method known in the art, such as described in T. W. Green et al., supra.

As an alternative to steps (a) to (c), pantothenic acid can be esterified with an alcohol of the formula R″OH, for example, by subjecting pantothenic acid to Fischer esterification conditions (i.e., excess alcohol, and catalytic acid under reflux).

The primary hydroxyl group on the compound formed in step (c) can be selectively phosphorylated. See J. D. Patrone, J. Yao, N. E. Scott, and G. D. Dotson, "Selective Inhibitors of Bacterial Phosphopantothenoylcysteine Synthetase", *J. Am. Chem. Soc.*, 2009, 131, 16340-16341). The conditions described in D. M. Lehsten, D. N. Baehr, T. J. Lobl, and A. R. Vaino, "An Improved Procedure for the Synthesis of Nucleoside Phosphoramidates", *Organic Process Research & Development*, 2002, 6, 819-822, can be used for this reaction.

This method is shown below with a method for preparing the phosphorylation reagent.

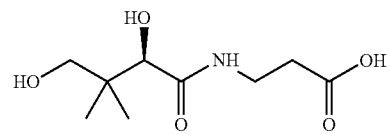

1

| PhCHO, ZnCl₂
| SOCl₂, R″OH
↓

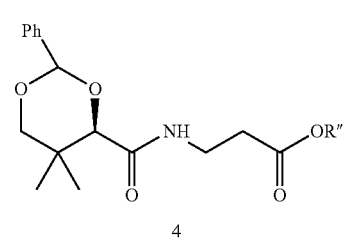
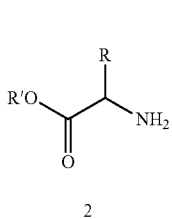
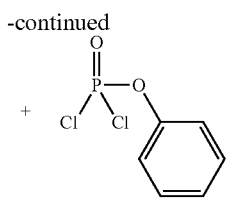

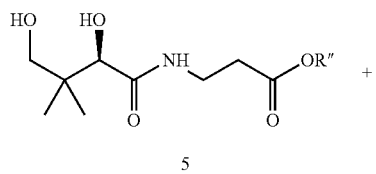

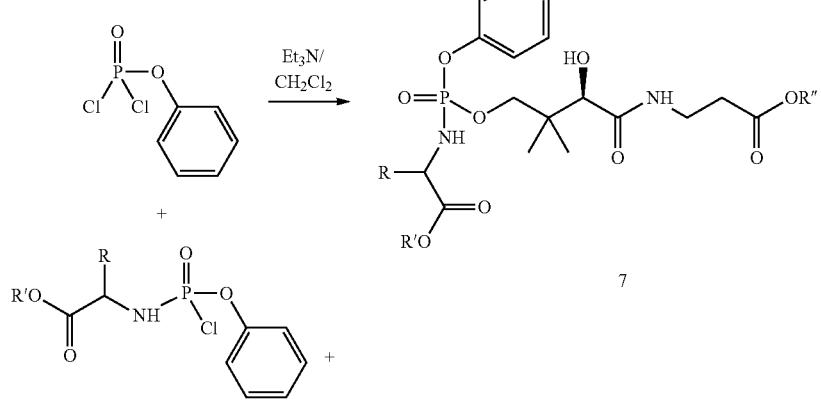

Optionally, an optically pure product can be obtained by performing a chiral separation of the final product, or one of the intermediates between steps in the synthesis.

Alternatively, the compounds of the present invention can be prepared by the route described in B. S. Ross, P. G. Reddy, H.-R. Zhang, S. Rachakonda, and M, J. Sofia, "Synthesis of Diastereomerically Pure Nucleotide Phosphoramidates", *J. Org. Chem.*, 2011, 76, 8311-8319. This route can produce an optically pure product without performing a final chiral separation step.

EXAMPLES

Example 1

Synthesis of ethyl 3-((2R)-4-(((((S)-1-ethoxy-1-oxo-propan-2-yl)amino)(phenoxy)phosphoryl)oxy)-2-hydroxy-3,3-dimethylbutanamido)propanoate

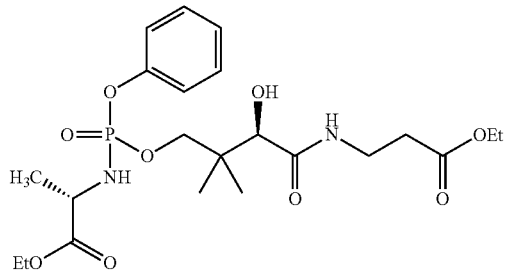 [SMILES: CCOC(=O)CCNC(=O)[C@H](O)C(C)(C)COP(=O)(N[C@@H](C)C(=O)OCC)Oc1ccccc1]

L-Alanine ethyl ester hydrochloride (0.50 g, 3.25 mmol) was suspended in 10 mL of $CH_2Cl_2$ and treated with phenyl phosphorodichloridate (0.50 mL, 3.35 mmol) at −10° C. and under an atmosphere of nitrogen. The well-stirred mixture was then treated dropwise with N-methylimidazole (1.0 mL, 12.5 mmol). After 1 hr. and still at −10° C., ethyl pantothenate (0.70 g, 2.8 mmol) in 3 mL of $CH_2Cl_2$ was added slowly. This mixture was allowed to warm to room temperature, and after 3 hrs, 2 mL of methanol was added. Extraction was performed sequentially with 1 M HCl, water, 5% $NaHCO_3$, and brine. The organic phase was dried ($Na_2SO_4$), and the solvent was evaporated affording 1.11 g of a clear, colorless syrup. This material was purified by flash column chromatography using 30 g of silica gel and eluting with 1:1 EtOAc/hexanes containing 5% EtOH. The process was repeated until 1.1 g of phosphoramidate was obtained. HPLC showed the product, as a 1:1 mixture of disastereomers, having a purity of 97%. $^1$H NMR (300 MHz, $CDCl_3$): δ 1.08 (s, 3H, $CH_3$), 1.21 (d, 3H, J=2.7 Hz, $CH_3$), 1.27 (m, 6H, $CH_3$), 1.35 (t, 3H, J=6.9 Hz, $CH_3$), 2.53 (q, 2H, J=4.2 Hz, $CH_2$), 3.50 (m, 2H, $CH_2$), 3.60 (m, 1H, CH), 3.78 (d, J=7.5 Hz, CH), 3.9 (m, 2H, $CH_2$), 4.10 (m, 6H, $CH_2$), 4.79 (t, 1H, J=6.5 Hz, CH), 7.15 and 7.40 (2 Ms, 5H, Ph). Expected Mol. Wt. 502.21, Observed Mol. Wt. 503.09 (M+H$^+$]

Example 2

Synthesis of methyl 3-((2R)-2-hydroxy-4-(((((S)-1-methoxy-1-oxopropan-2-yl)amino)(phenoxy)phosphoryl)oxy)-3,3-dimethylbutanamido)propanoate

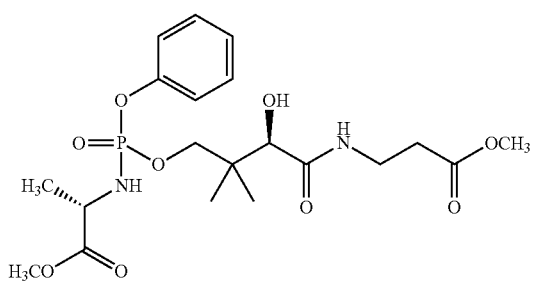 [SMILES: COC(=O)CCNC(=O)[C@H](O)C(C)(C)COP(=O)(N[C@@H](C)C(=O)OC)Oc1ccccc1]

L-alanine methyl ester hydrochloride (1.35 g, 9.65 mmol) was suspended in dichloromethane (20 mL) and treated with phenyl phosphodichloridate (1.51 mL, 10.15 mmol) at −78° C. under an atmosphere of argon. Diisopropylethylamine (2.6 mL, 20.27 mmol) was added dropwise. The mixture was stirred at −78° C. for 30 minutes, then allowed to warm to room temperature for 1 hr. The mixture was chilled to −5° C. and methyl pantothenate (1.6 mL, 20.27 mmol) was added dropwise in dichloromethane. N-methylimidazole (1.6 mL, 20.27 mmol) was added, and after stirring at −5° C. for 30 mins and room temperature for 1 hour, 2 mL of methanol was added. The mixture was washed sequentially with water (30 mL), 5% citric acid (30 mL), and brine (10 mL). The organic phase was dried ($Na_2SO_4$) and the solvent was removed under reduced pressure. Purification was achieved with a 1:1 mixture of EtOAc:hexane to afford the product as a clear colorless oil. (1.1 g, 24% yield). HPLC showed the product, as a 1:1 mixture of diastereomers, having a purity of 97%. $^1$H NMR (300 MHz, $CDCl_3$): δ 1.11 (s, 3H, $CH_3$), 1.27, 1.39 and 1.40 (2 Ss, 3H, $CH_3$), 1.41 (overlapping d, 3H, J=1.2 Hz, $CHCH_3$), 3.55 (m, 2H, $CH_2$), 3.60 (m, 1H, $CH_2$), 3.63 (m, 1H, CH), 3.66 and 3.68 (2 Ss, 3H, $COCH_3$), 3.70 and 3.74 (2 Ss, 3H, $COCH_3$), 3.78 (m, 1H CH), 4.03 (m, 1H, CH), 4.17 (m, 1H, CH), 7.16 and 7.35 and 7.40 (2 Ms, 5H, Ph). Expected Mol. Wt. 474.18, Observed Mol. Wt. 475.03 (M+H$^+$].

Examples 3-14

The compounds shown in the table below were prepared according to the synthetic procedures outlined in Examples 1 and 2, using the appropriate starting materials.

Example 15

In Vitro Bacterial Testing

SJ16 is a strain of Escherichia coli that requires addition of pantothenic acid to proliferate (i.e., it has a mutation such that pantothenic acid is inactive). Thus, it serves as a useful assay in determining whether a compound can rescue an organism deficient in PANK, the cause of PKAN. Compounds of the present invention were tested for toxicity and for the ability to support growth of Escherichia coli K-12 strains SJ16 (see, e.g., Jackowski et al., J. Bacteriol., 148, 926-932, 1981) and DV70 (see, e.g., Vallari et al., J. Bacteriol., 169, 5795-5800, 1987) under permissive and non-permissive conditions. The test compound in a solvent (dimethylsulfoxide, DMSO) was added to growth medium at a final concentration of 8 µM. Solvent alone (DMSO) was added to the growth medium at a final concentration ≤0.1% as a control.

Strain SJ16 was grown at 37° C. for 18 hours on a solid medium containing agar (1.5%), M9 minimal essential salts (see, Miller, Experiments in Molecular Genetics. Cold Spring Harbor Laboratory, Cold Spring Harbor, N.Y., 1972), glucose (0.4%), methionine (50 µg/ml), and with (permissive) or without (non-permissive) calcium pantothenate (1 µM). Lack of growth with calcium pantothenate supplementation indicated toxicity. Growth without calcium pantothenate supplementation indicated the ability of the bacteria to metabolize the compound to yield pantothenate or β-alanine.

Strain DV70 was grown at 30° C. (permissive) or 42° C. (non-permissive) for 18 hours on solid medium containing agar (1.5%), M9 minimal essential salts, glucose (0.4%), methionine (50 µg/ml), and calcium pantothenate (1 µM). Lack of growth at 30° C. indicated toxicity. Growth at 42° C. indicated metabolism of the compound and subsequent conversion to coenzyme A by the bacteria.

SJ16 recovery results for the compounds of Examples 2, 5, 7 and 12 are shown in the Table below. A "Yes" result indicates that bacteria were alive after 18 hours. The compounds of Examples 2, 5, 7 and 12 did not result in recovery of the DV70 strain.

| Example | DMSO Used | SJ16 Recovery |
|---|---|---|
| 2 | <10% | Yes |
| 5 | >50% | Yes |
| 7 | >60% | Yes |
| 12 | >70% | Yes* |

*test compound precipitated

| Example | R (Amino Acid) | R' | R" | Mass Isolated (g) | Purity (%) | Expected Mol. Wt. | Observed Mol. Wt. [M + H$^+$] |
|---|---|---|---|---|---|---|---|
| 3 | Me (L-Ala) | n-Bu | n-Bu | 0.34 | 91 | 558.27 | 559.24 |
| 4 | Me (L-Ala) | Bn | Et | 1.87 | 97 | 564.22 | 565.07 |
| 5 | Me (L-Ala) | Et | Bn | 1.36 | 97 | 564.22 | 565.14 |
| 6 | Me (L-Ala) | Bn | Bn | 1.38 | 98 | 626.24 | 627.32 |
| 7 | Me (L-Ala) | MeCyPr | MeCyPr | 1.77 | 100 | 554.24 | 555.23 |
| 8 | H (Gly) | Bn | Et | 0.44 | 93 | 550.21 | 551.02 |
| 9 | i-Pr (L-Val) | Et | Et | 0.39 | 94 | 530.24 | 531.14 |
| 10 | MeIndole (L-Trp) | Me | Me | 1.43 | 95 | 589.22 | 590.16 |
| 11 | MeIndole (L-Trp) | Et | Et | 0.45 | 95 | 617.25 | 618.21 |
| 12 | MeIndole (L-Trp) | Bn | Et | 0.47 | 91 | 679.27 | 680.17 |
| 13 | MeIndole (L-Trp) | Et | Bn | 1.33 | 95 | 679.27 | 680.17 |
| 14 | MeIndole (L-Trp) | Bn | Bn | 0.13 | 90 | 741.28 | 742.24 |

Example 16

The compounds of Examples 2, 5, 7 and 12 were tested in immortalized human cells (HEK 293T). The amount of acetyl-CoA (the downstream result of PANK) following administration of the compounds of Examples 2, 5, 7 and 12 were measured by mass spectrometry. The results are shown in FIG. 1.

As can be seen from FIG. 1, treatment of HEK 293T cells with 200 μM of the compound of Example 2 afforded a 42% increase in acetyl CoA over baseline (p<0.0005). Treatment of HEK 293T cells with 20 μM of the compound of Example 7 afforded a 38% increase in acetyl CoA over baseline (p<0.005).

Example 17

In Vivo Testing

Compounds of the invention were tested for efficacy in Pank1$^{-/-}$ mice (strain 129SvJ×C57BL/6J background) which were compared with age-matched Pank1$^{+/+}$ (strain 129SvJ× C57BL/6J) littermates, ages 8-12 weeks. Each mouse was identified with a coded ear tag and weighed on the first day of testing. Each compound was administered to 4-5 mice by intraperitoneal injection at a dose of 1.2 μmoles/g body weight in 5 μL dimethylsulfoxide once daily for 5 days, and mice were then fasted overnight, weighed and euthanized. Untreated mice received 5 μL dimethylsulfoxide once daily for 5 days and then were fasted overnight prior to weighing and euthanasia. Livers were excised from each mouse, aliquots were snap-frozen in liquid nitrogen, and stored at −80° C. Within 7 days, liver samples were thawed on ice, weighed and analyzed for coenzyme A content as described below. Efficacy was indicated by a statistically significant increase in the liver Coenzyme A levels in the Pank1$^{-/-}$ mice as compared to the liver from untreated Pank1$^{-/-}$ mice and by equivalence in comparison with Coenzyme A levels in untreated Pank1$^{+/+}$ mice.

CoA Measurements: Extraction of Fibroblasts and Liver and Derivatization of Coenzyme A Prior to High Pressure Liquid Chromatography (HPLC)

Extraction of fibroblasts or liver was performed by modification of a method described previously (see, Minkler et al., *Anal. Biochem.*, 376, 275-276, 2008). Coenzyme A derivatization was performed by modification of a method described previously (see, Shimada et al., *J. Chromatogr. B Biomed. Appl.*, 659, 227-241, 1994).

Liver (20-50 mg) was homogenized in 2 mL of 1 mM KOH, and the pH was adjusted to 12 with 0.25 M KOH. Fibroblasts were scraped off the culture dish and collected in 1 mL of water, which was transferred to 200 μL of 0.25 M NaOH. The liver homogenate was then incubated at 55° C. for 2 hours and the fibroblast cells were incubated for 1 hour at 55° C. The pH was adjusted to pH 8 with 1 M Trizma-HCl, and 10 μL of 100 mM monobromobimane (mBBr, Life Technologies, NY) was added for 2 hours in the dark. The reaction was acidified with acetic acid, and centrifuged at 500 g for 15 minutes. The supernatant was then added to a 2-(2-pyridyl) ethyl column (Supelco) which was equilibrated with 1 mL of 50% methanol/2% acetic acid. The column was washed with 2×1 mL 50% methanol/2% acetic acid and 1 mL water. Samples were eluted with 2×1 mL 50 mM ammonium formate in 95% ethanol. Samples were evaporated under nitrogen and resuspended in 300 μL of water. Samples were spun through a Spin-X Centrifuge Tube Filter (0.22 μm Cellulose Acetate, Costar) to remove any precipitants before HPLC.

Coenzyme A Quantification by HPLC

The mBBr derivative of Coenzyme A was separated by reverse-phase HPLC using a Gemini $C_{18}$ 3 μm column (150× 4.60 mm) from Phenomenex (Torrance, Calif.). The chromatography system used was a Waters e2695 separation module with a UV/Vis detector and controlled by the Empower 3 software. Solvent A was 50 mM potassium phosphate pH 4.6, and solvent B was 100% acetonitrile. 20 μL of sample was injected onto the column, and the flow rate was 0.5 mL/min. The HPLC program was the following: starting solvent mixture of 90% A/10% B, 0 to 2 min isocratic with 10% B, 2 to 9 min linear gradient from 10% B to 25% B, 9 to 23 min concave gradient from 25% B to 40% B, 23 to 25 min linear gradient from 40% to 10%, and 25 to 30 min isocratic with 10% B. The detector was set at λ393 nm. The area under the mBBr derivatized Coenzyme A peak was integrated and was compared to a standard concentration curve of mBBr-Coenzyme A prepared from commercial Coenzyme A.

Figure 2:
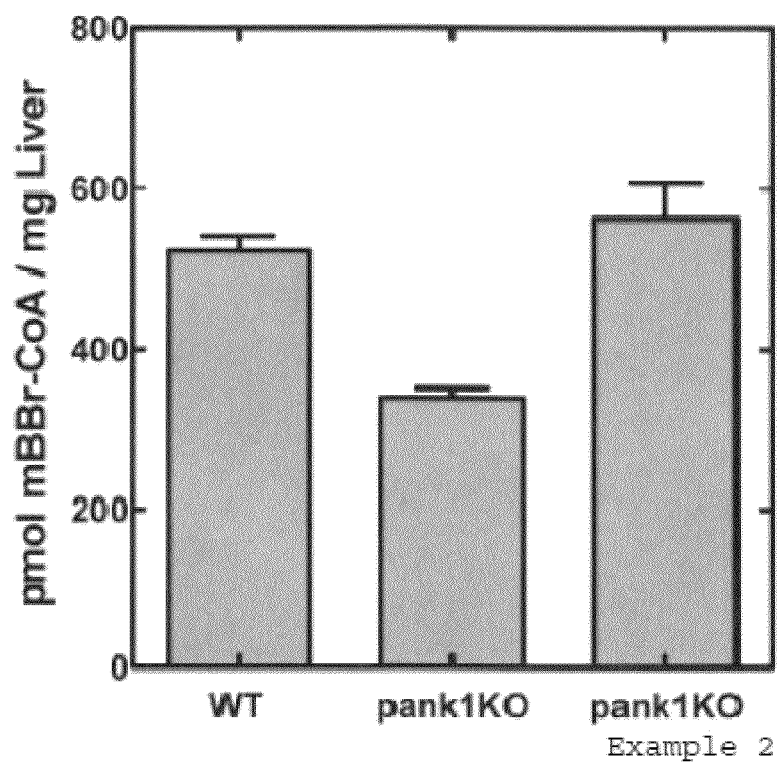
FIG. 2 is a bar graph showing levels of mBBr CoA in untreated Pank$^{1+/+}$ mice (WT), untreated Pank$^{1-/-}$ knock out mice (pank1KO) and PANK knockout mice following administration of the compound of Example 2 (Pank KO+Example 2).

FIG. 2 depicts levels of mBBr CoA in PANK knockout mice following administration of the compound of Example 2. As can be seen from FIG. 2, the compound of Example 2 restored levels of CoA to those seen in normal mice. This is also shown in the Table below.

|  | pmol mBBR-CoA/mg Liver | | |
| --- | --- | --- | --- |
|  | Mean | SEM | n |
| WT | 522.545 | 18.279 | 4 |
| pank1 KO | 339.560 | 11.496 | 5 |
| pank 1 KO + Example 2 | 563.358 | 44.959 | 5 |

All publications, patents, and patent applications cited herein are hereby incorporated by reference.

What is claimed is:

1. A method of treating pantothenate kinase-associated neurodegeneration in a subject,
the method comprising administering to the subject an effective amount of a compound of the following formula:

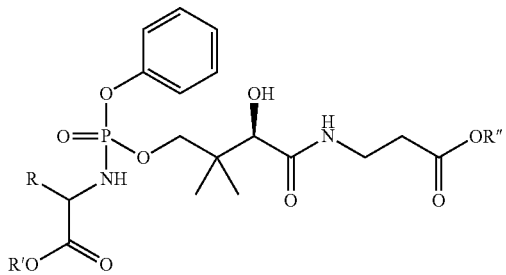

or a pharmaceutically acceptable salt thereof, wherein R, R' and R" are selected from the group consisting of:

| R (Amino Acid) | R' | R" |
| --- | --- | --- |
| Me (L-Ala) | Me | Me |
| Me (L-Ala) | Et | Bn |
| Me (L-Ala) | MeCyPr | MeCyPr |
| MeIndole (L-Trp) | Bn | Et. |

2. The method of claim 1, wherein R, R' and R" are methyl.

3. The method of claim 1, wherein R is methyl, R' is ethyl and R" is benzyl.

4. The method of claim 1, wherein R is methyl, and R' and R" are methylcyclopropyl.

5. The method of claim 1, wherein R is 1H-indol-3yl-methyl, R' is benzyl and R" is ethyl.

6. The method of claim 1, wherein the subject is a child.

7. The method of claim 6, wherein the child is 10 to 15 years old.

8. The method of claim 1, wherein the subject is an adult.

9. A method of treating a subject having neuronal cells with an over accumulation of iron, the method comprising administering to the subject an effective amount of a compound of the following formula:

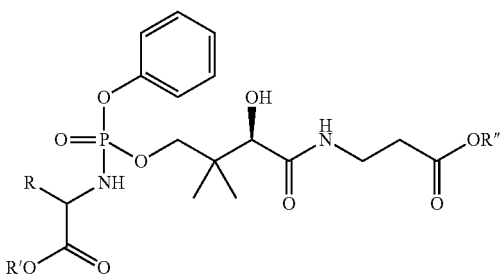

or a pharmaceutically acceptable salt thereof, wherein R, R' and R" are selected from the group consisting of:

| R (Amino Acid) | R' | R" |
| --- | --- | --- |
| Me (L-Ala) | Me | Me |
| Me (L-Ala) | Et | Bn |
| Me (L-Ala) | MeCyPr | MeCyPr |
| MeIndole (L-Trp) | Bn | Et. |

10. The method of claim 9, wherein R, R' and R" are methyl.

11. The method of claim 9, wherein R is methyl, R' is ethyl and R" is benzyl.

12. The method of claim 9, wherein R is methyl, and R' and R" are methylcyclopropyl.

13. The method of claim 9, where R is 1H-indol-3yl-methyl, R' is benzyl and R" is ethyl.

14. The method of claim 9, wherein the subject is a child.

15. The method of claim 14, wherein the child is 10 to 15 years old.

16. The method of claim 9, wherein the subject is an adult.

17. The method of claim 9, wherein the subject suffers from pantothenate kinase-associated neurodegeneration.

18. A method of treating Parkinson's disease, dystonia, extrapyramidal effects, dysphagia, rigidity and/or stiffness of limbs, choreoathetosis, tremor, spasticity, muscle weakness, or seizure in a subject, the method comprising administering to the subject an effective amount of a compound of the following formula:

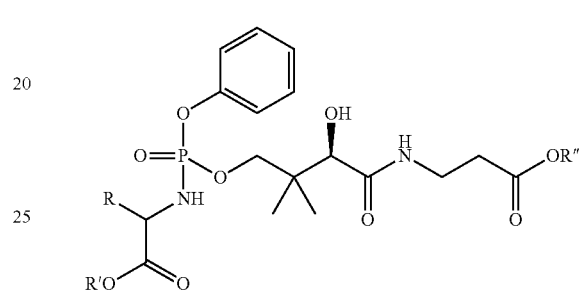

or a pharmaceutically acceptable salt thereof, wherein R, R' and R" are selected from the group consisting of:

| R (Amino Acid) | R' | R" |
| --- | --- | --- |
| Me (L-Ala) | Me | Me |
| Me (L-Ala) | Et | Bn |
| Me (L-Ala) | MeCyPr | MeCyPr |
| MeIndole (L-Trp) | Bn | Et. |

19. The method of claim 18, wherein R, R' and R" are methyl.

* * * * *